(12) United States Patent
Vodak et al.

(10) Patent No.: US 11,364,203 B2
(45) Date of Patent: Jun. 21, 2022

(54) PROCESS FOR FORMING ACTIVE DOMAINS DISPERSED IN A MATRIX

(71) Applicant: Bend Research, Inc., Bend, OR (US)

(72) Inventors: David Thomas Vodak, Bend, OR (US); Dwayne Thomas Friesen, Bend, OR (US)

(73) Assignee: Bend Reserch, Inc., Bend, OR (US)

( * ) Notice: Subject to any disclaimer, the term of this patent is extended or adjusted under 35 U.S.C. 154(b) by 220 days.

(21) Appl. No.: 15/523,171

(22) PCT Filed: Oct. 5, 2015

(86) PCT No.: PCT/IB2015/057601
§ 371 (c)(1),
(2) Date: Apr. 28, 2017

(87) PCT Pub. No.: WO2016/067132
PCT Pub. Date: May 6, 2016

(65) Prior Publication Data
US 2018/0015041 A1 Jan. 18, 2018

Related U.S. Application Data

(60) Provisional application No. 62/073,878, filed on Oct. 31, 2014.

(51) Int. Cl.
*A61K 9/16* (2006.01)
*A61K 31/216* (2006.01)
(Continued)

(52) U.S. Cl.
CPC .......... *A61K 9/1694* (2013.01); *A61K 9/1623* (2013.01); *A61K 31/216* (2013.01); *A61K 31/56* (2013.01); *B01J 2/02* (2013.01)

(58) Field of Classification Search
CPC .................... A61K 9/1694; A61K 9/1623
(Continued)

(56) References Cited

U.S. PATENT DOCUMENTS

| 2,460,546 A | 2/1949 | Stephanoff |
| 2,937,091 A | 5/1960 | Rosenberg |

(Continued)

FOREIGN PATENT DOCUMENTS

| DE | 3229843 A1 | 3/1983 |
| EP | 0113967 A2 | 7/1984 |

(Continued)

OTHER PUBLICATIONS

Acetone Compound Summary, PubChem, U.S. National Library of Medicine, National Center for Biotechnology Information, https://pubchem.ncbi.nlm.nih.gov/compound/acetone (Year: 2019).*

(Continued)

*Primary Examiner* — Michael H. Wilson
*Assistant Examiner* — Russell E Sparks
(74) *Attorney, Agent, or Firm* — Klarquist Sparkman, LLP

(57) ABSTRACT

Disclosed are processes for forming compositions comprising small domains of an active agent and a matrix material, and methods of using them. A suspension of an active agent, a matrix material, a first solvent, and a second solvent is formed at a temperature $T_1$, heated to a temperature $T_2$ and spray dried.

15 Claims, 6 Drawing Sheets

Example 1

Example 2

Example 3

(51) Int. Cl.
*A61K 31/56* (2006.01)
*B01J 2/02* (2006.01)

(58) Field of Classification Search
USPC .......................................................... 264/12
See application file for complete search history.

(56) References Cited

U.S. PATENT DOCUMENTS

| | | | |
|---|---|---|---|
| 3,557,864 A | 1/1971 | Berg | |
| 3,621,902 A | 11/1971 | Okada et al. | |
| 3,673,106 A | 6/1972 | Jonas et al. | |
| 3,922,189 A | 11/1975 | Penders | |
| 3,990,938 A | 11/1976 | Whitehouse | |
| 4,019,958 A | 4/1977 | Hell et al. | |
| 4,089,120 A | 5/1978 | Kozischek | |
| 4,201,756 A | 5/1980 | Saeman et al. | |
| 4,209,912 A | 7/1980 | Barker | |
| 5,013,557 A | 5/1991 | Tai | |
| 5,039,532 A | 8/1991 | Jost et al. | |
| 5,135,611 A | 8/1992 | Cameron | |
| 6,165,506 A | 12/2000 | Jain et al. | |
| RE37,053 E | 2/2001 | Hanes et al. | |
| 6,406,735 B2 | 6/2002 | Stein et al. | |
| 6,572,893 B2 | 6/2003 | Gordon et al. | |
| 6,589,557 B2 | 7/2003 | Straub et al. | |
| 6,589,562 B1 | 7/2003 | Shefer et al. | |
| 6,610,317 B2 | 8/2003 | Straub et al. | |
| 6,740,631 B2 | 5/2004 | Shefer et al. | |
| 6,800,297 B2 | 10/2004 | Altreuter et al. | |
| 6,932,983 B1 | 8/2005 | Straub et al. | |
| 6,942,868 B2 | 9/2005 | Edwards et al. | |
| 6,977,087 B2 | 12/2005 | Edwards et al. | |
| 6,998,393 B2 | 2/2006 | Jin et al. | |
| 7,018,657 B2 | 3/2006 | Dickinson et al. | |
| 7,078,057 B2 | 7/2006 | Kerkhof | |
| 7,300,919 B2 | 11/2007 | Patton | |
| 7,323,441 B2 | 1/2008 | Morazzoni et al. | |
| 7,378,110 B2 | 5/2008 | Truong Le et al. | |
| 7,404,828 B1 | 7/2008 | Nicola | |
| 7,521,069 B2 | 4/2009 | Patton et al. | |
| 7,682,635 B2 | 3/2010 | Gref et al. | |
| 7,780,988 B2 | 8/2010 | Beyerinck et al. | |
| 7,858,609 B2 * | 12/2010 | Shaw | A61K 9/10 514/183 |
| 7,928,089 B2 | 4/2011 | Morton et al. | |
| 7,967,221 B2 * | 6/2011 | Snyder | B05B 7/0416 239/418 |
| 8,007,831 B2 * | 8/2011 | Lewis | A61K 9/0019 424/501 |
| 8,257,739 B2 | 9/2012 | Babcock et al. | |
| 8,263,128 B2 | 9/2012 | Curatolo et al. | |
| 8,343,550 B2 | 1/2013 | Beyerinck et al. | |
| 8,402,672 B2 | 3/2013 | Nielsen | |
| 8,491,933 B2 | 7/2013 | Babcock et al. | |
| 8,668,934 B2 | 3/2014 | Vehring et al. | |
| 8,828,438 B2 | 9/2014 | Friesen et al. | |
| 8,834,929 B2 | 9/2014 | Dobry et al. | |
| 8,974,827 B2 | 3/2015 | Bloom et al. | |
| 9,084,944 B2 | 7/2015 | Dobry et al. | |
| 9,084,976 B2 | 7/2015 | Dobry et al. | |
| 9,233,078 B2 | 1/2016 | Bloom et al. | |
| 9,248,584 B2 | 2/2016 | Friesen et al. | |
| 9,265,731 B2 | 2/2016 | Ray et al. | |
| 9,545,384 B2 | 1/2017 | Miller | |
| 2001/0053791 A1 | 12/2001 | Babcock et al. | |
| 2002/0031547 A1 | 3/2002 | Takagi et al. | |
| 2002/0146509 A1 | 10/2002 | Kodokian et al. | |
| 2003/0017214 A1 | 1/2003 | Sherman | |
| 2003/0104076 A1 | 6/2003 | Berkulin et al. | |
| 2003/0124193 A1 | 7/2003 | Snyder et al. | |
| 2003/0166509 A1 | 9/2003 | Edwards et al. | |
| 2003/0185893 A1 | 10/2003 | Beyerinck et al. | |
| 2003/0207776 A1 | 11/2003 | Shefer et al. | |
| 2003/0215515 A1 | 11/2003 | Truong-Le et al. | |
| 2004/0006276 A1 | 1/2004 | Demos et al. | |
| 2004/0037905 A1 | 2/2004 | Bringe | |
| 2004/0062778 A1 | 4/2004 | Shefer et al. | |
| 2004/0076670 A1 | 4/2004 | Klinksiek et al. | |
| 2004/0091535 A1 | 5/2004 | Vachon et al. | |
| 2004/0092470 A1 | 5/2004 | Leonard et al. | |
| 2004/0109894 A1 | 6/2004 | Shefer et al. | |
| 2004/0145069 A1 | 7/2004 | Low | |
| 2004/0176391 A1 | 9/2004 | Weers et al. | |
| 2004/0184995 A1 | 9/2004 | Katsuma et al. | |
| 2004/0191186 A1 | 9/2004 | Edwards et al. | |
| 2004/0224019 A1 | 11/2004 | Shefer et al. | |
| 2004/0234597 A1 | 11/2004 | Shefer et al. | |
| 2005/0019270 A1 | 1/2005 | Finlay et al. | |
| 2005/0031692 A1 | 2/2005 | Beyerinck et al. | |
| 2005/0037996 A1 | 2/2005 | Beck et al. | |
| 2005/0058710 A1 | 3/2005 | Straub et al. | |
| 2005/0065047 A1 | 3/2005 | Shefer et al. | |
| 2005/0112235 A1 | 5/2005 | Shefer et al. | |
| 2005/0118208 A1 | 6/2005 | Bewert et al. | |
| 2005/0158249 A1 | 7/2005 | Edwards et al. | |
| 2005/0191246 A1 | 9/2005 | Bechtold-Peters et al. | |
| 2006/0018942 A1 * | 1/2006 | Rowe | A61K 9/0024 424/422 |
| 2006/0039987 A1 | 2/2006 | Batycky et al. | |
| 2006/0068019 A1 | 3/2006 | Dalziel et al. | |
| 2006/0093557 A1 | 5/2006 | Dickinson et al. | |
| 2006/0127480 A1 | 6/2006 | Tobyn et al. | |
| 2006/0142185 A1 | 6/2006 | Morazzoni et al. | |
| 2006/0153912 A1 | 7/2006 | Habich et al. | |
| 2006/0159625 A1 | 7/2006 | Tarara et al. | |
| 2006/0165785 A1 | 7/2006 | Noga et al. | |
| 2006/0210640 A1 | 9/2006 | Kerkhof | |
| 2006/0216351 A1 | 9/2006 | Friesen et al. | |
| 2006/0263454 A1 | 11/2006 | Sugiyama et al. | |
| 2006/0280691 A1 | 12/2006 | Wang et al. | |
| 2006/0292081 A1 | 12/2006 | Morton et al. | |
| 2007/0020197 A1 | 1/2007 | Galli et al. | |
| 2007/0031490 A1 | 2/2007 | Loebenberg et al. | |
| 2007/0042021 A1 | 2/2007 | Schiffrin et al. | |
| 2007/0043030 A1 | 2/2007 | Morton et al. | |
| 2007/0045100 A1 | 3/2007 | Wright | |
| 2007/0081947 A1 | 4/2007 | Eble et al. | |
| 2007/0134341 A1 | 6/2007 | Kipp et al. | |
| 2007/0148236 A1 | 6/2007 | Babcock et al. | |
| 2007/0166386 A1 | 7/2007 | Chinea et al. | |
| 2007/0189979 A1 | 8/2007 | Zeng et al. | |
| 2007/0225337 A1 | 9/2007 | Greil et al. | |
| 2008/0057003 A1 | 3/2008 | Bechtold-Peters et al. | |
| 2008/0124349 A1 | 5/2008 | Engstad et al. | |
| 2008/0131514 A1 | 6/2008 | Truong-Le et al. | |
| 2008/0181962 A1 | 7/2008 | Brzeczko et al. | |
| 2008/0207476 A1 | 8/2008 | Artiga Gonzalez et al. | |
| 2008/0229609 A1 | 9/2008 | Bronshtein | |
| 2008/0248117 A1 | 10/2008 | Kolter et al. | |
| 2008/0292707 A1 | 11/2008 | Babcock et al. | |
| 2009/0038612 A1 | 2/2009 | Nilsson et al. | |
| 2009/0142404 A1 | 6/2009 | Appel et al. | |
| 2009/0269411 A1 | 10/2009 | Bellinghausen et al. | |
| 2009/0270308 A1 | 10/2009 | Libin et al. | |
| 2009/0285905 A1 | 11/2009 | Gordon et al. | |
| 2012/0015924 A1 | 1/2012 | Friesen et al. | |
| 2015/0216813 A1 | 8/2015 | Everett et al. | |
| 2018/0071215 A1 * | 3/2018 | Trout | A61K 31/216 |

FOREIGN PATENT DOCUMENTS

| | | |
|---|---|---|
| EP | 0380219 A2 | 1/1989 |
| EP | 0405598 A2 | 1/1991 |
| EP | 0421581 A1 | 4/1991 |
| EP | 0421582 A1 | 4/1991 |
| EP | 0807431 A2 | 11/1997 |
| EP | 1239844 A1 | 9/2002 |
| EP | 1506996 A2 | 2/2005 |
| EP | 1552815 A1 | 7/2005 |
| EP | 1552817 A1 | 7/2005 |
| EP | 1741424 A2 | 1/2007 |
| EP | 1844758 A1 | 10/2007 |
| GB | 918168 A | 2/1963 |
| GB | 1305598 A | 2/1973 |

(56) References Cited

FOREIGN PATENT DOCUMENTS

| | | | | |
|---|---|---|---|---|
| GB | 2132495 | A | 7/1984 | |
| WO | WO1991/012074 | A1 | 8/1991 | |
| WO | WO-0033817 | A1 * | 6/2000 | ............... A61P 3/02 |
| WO | WO2000/072827 | A2 | 12/2000 | |
| WO | WO2001/045674 | A1 | 6/2001 | |
| WO | WO2001/045677 | A1 | 6/2001 | |
| WO | WO2001/095877 | A2 | 12/2001 | |
| WO | WO2002/024169 | A1 | 3/2002 | |
| WO | WO2003/043586 | A2 | 5/2003 | |
| WO | WO2003/092659 | A1 | 11/2003 | |
| WO | WO 03/099290 | A1 | 12/2003 | |
| WO | WO2003/105780 | A2 | 12/2003 | |
| WO | WO2004/012690 | A1 | 2/2004 | |
| WO | WO2004/030659 | A1 | 4/2004 | |
| WO | WO2004/039960 | A2 | 5/2004 | |
| WO | WO2004/041991 | A1 | 5/2004 | |
| WO | WO2004/060351 | A2 | 7/2004 | |
| WO | WO2004/082660 | A1 | 9/2004 | |
| WO | WO2005/011636 | | 2/2005 | |
| WO | WO2005/055976 | A2 | 6/2005 | |
| WO | WO2005/115330 | | 12/2005 | |
| WO | WO2005/117962 | A1 | 12/2005 | |
| WO | WO2006/003504 | A1 | 1/2006 | |
| WO | WO2006/036617 | A1 | 4/2006 | |
| WO | WO 2008/012617 | A1 | 1/2008 | |
| WO | WO2008/092057 | A2 | 7/2008 | |
| WO | WO2008/101173 | A2 | 8/2008 | |
| WO | WO2009/046440 | A1 | 4/2009 | |
| WO | WO2010/102066 | | 9/2010 | |
| WO | WO2010/132827 | | 11/2010 | |
| WO | WO-2012031129 | A2 * | 3/2012 | ............... B01J 2/04 |
| WO | WO2016/012906 | | 1/2016 | |
| WO | WO2016/063157 | | 4/2016 | |

OTHER PUBLICATIONS

Light Petroleum, Joint Expert Committee on Food Additives, Food and Agriculture Organization of the United Nations, http://www.fao.org/fileadmin/user_upload/jecfa_additives/docs/Monograph1/Additive-252.pdf (Year: 2004).*

Petroleum Ether Material Safety Data Sheet, ScholAR Chemistry, https://www.mccsd.net/cms/lib/NY02208580/Centricity/Shared/Material%20Safety%20Data%20Sheets%20_MSDS_/MSDS%20Sheets_Petroleum_Ether_518_00.pdf (Year: 2009).*

Vapor-Liquid Equilibrium Data, Dortmund Data Bank, http://www.ddbst.com/en/EED/VLE/VLE%20Acetone%3BWater.php (Year: 2020).*

Vapor Liquid Equilibrium Data, Dortmund Data Bank, http://www.ddbst.com/en/EED/VLE/VLE%20Tetrahydrofuran%3BWater.php (Year: 2020).*

Helmenstine, Anne M. "Boiling Points of Ethanol, Methanol, and Isopropyl Alcohol." ThoughtCo, Dotdash, May 31, 2019, www.thoughtco.com/boiling-point-of-alcohol-608491#:~:text=The%20boiling%20point%20of%20ethanol,173.1%20F%20(78.37%20C). (Year: 2019).*

Vapor-Liquid Equilibrium Data, Dortmund Data Bank, http://www.ddbst.com/en/EED/VLE/VLE%20Ethanol%3BWater.php (Year: 2021).*

International Search Report and Written Opinion, dated Dec. 15, 2015, issued in corresponding International Application No. PCT/IB2015/057601.

Office Action dated Nov. 29, 2018 for U.S. Appl. No. 15/520,812, 15 pp.

Kawashima et al., "A New Powder Design Method to Improve Inhalation Efficiency of Pranlukast Hydrate Dry Powder Aerosols by Surface Modification with Hydroxypropylmethylcellulose Phthalate Nanospheres," Pharmaceutical Research, vol. 15, No. 11, pp. 1748-1752 (Nov. 1998).

Rasenack et al., "Micronization of Anti-Inflammatory Drugs for Pulmonary Delivery by a Controlled Crystallization Process," Journal of Pharmaceutical Sciences, vol. 92, No. 1, pp. 35-44 (Jan. 2003).

Sarkari et al., "Enhanced drug dissolution using evaporative precipitation into aqueous solution," International Journal of Pharmaceutics, vol. 243, Issues 1-2, pp. 17-31 (Aug. 2002).

Steckel et al., "In-situ-micronization of disodium cromoglycate for pulmonary delivery," European Journal of Pharmaceutics and Biopharmaceutics, vol. 55, No. 2, pp. 173-180 (Mar. 2003).

Steckel et al., "In vitro characterization of jet-milled and in-situ-micronized fluticasone-17-propionate," International Journal of Pharmaceutics, vol. 258, Issues 1-2, pp. 65-75 (Jun. 2003).

Sham et al., "Formulation and characterization of spray-dried powders containing nanoparticles for aerosol delivery to the lung," International Journal of Pharmaceutics, vol. 269, Issue 2, pp. 457-467 (Jan. 2004).

Snyder, Herman E., "Streamlining Spray Drying Process Design for Pulmonary Dry Powder Product Development: Application of Computational Fluid Dynamics to Aid System Scale-Up," *Respiratory Drug Delivery*, 2008, pp. 207-215.

Office Action, dated Sep. 13, 2019, issued in related European Patent Application No. 15 781 151.4, 6 pages.

Tetrahydrofuran 109-99-9, CAS DataBase List, *ChemicalBook* database (chemicalbook.com), downloaded Dec. 7, 2020, 2 pages.

Tetrahydrofuran, PubChem CID 8028, modified Dec. 5, 2020, 7 pages.

* cited by examiner

PROCESS FOR FORMING ACTIVE DOMAINS DISPERSED IN A MATRIX

CROSS REFERENCE TO RELATED APPLICATIONS

This is the U.S. National Stage of International Application No. PCT/IB2015/057601, filed Oct. 5, 2015, which was published in English under PCT Article 21(2), which in turn claims the benefit of U.S. Provisional Application No. 62/073,878, filed Oct. 31, 2014.

FIELD

Disclosed are processes for forming compositions comprising small domains of active agent and a matrix material, and methods of using them.

BACKGROUND

Solid compositions of a low-solubility drug and a concentration-enhancing polymer wherein the drug is in a semi-ordered state can be made by forming a solid amorphous dispersion of the drug and the concentration-enhancing polymer followed by treating the dispersion by (1) heating the dispersion; (2) exposing the dispersion to a mobility enhancing agent; and/or (3) a combination of (1) and (2).

SUMMARY

Disclosed is a spray drying process for forming a composition of an active agent and a matrix material. The process comprises (a) forming a suspension at a temperature $T_1$ comprising said active, said matrix material, a first solvent, and a second solvent; (b) heating the suspension to a temperature $T_2$, which is greater than $T_1$, and a pressure $P_1$, such that said active agent and said matrix material are soluble in the first solvent and the second solvent so as to form a spray solution. The spray solution is atomized to form droplets. At least a portion of the first solvent and the second solvent is removed to form solid particles and collecting the solid particles having active-rich domains and active-poor domains. The solubility of the matrix material in the first solvent at $T_2$ is greater than the solubility of the matrix material in the second solvent at $T_2$, the solubility of the active in the second solvent at $T_2$ is greater than the solubility of the active in the first solvent at $T_2$. The ambient-pressure boiling point of the first solvent is greater than the ambient-pressure boiling point of the second solvent.

In one embodiment, the second solvent evaporates more quickly from the droplets than the first solvent so that said active precipitates during the drying of said droplet at a rate that is initially faster than the rate at which the matrix precipitates, leading to active-rich domains and active poor domains in the droplets.

In independent embodiments, the ambient-pressure boiling point of the first solvent is at least 10° C. greater than the ambient-pressure boiling point of the second solvent. In another embodiment, the ambient-pressure boiling point of the first solvent is at least 20° C. greater than the ambient-pressure boiling point of the second solvent.

In any or all of the above embodiments, the matrix material has a solubility in the first solvent that is at least 2-fold the solubility of the matrix material in the second solvent. In any or all the above embodiments, the matrix material has a solubility in the first solvent that is at least 5-fold the solubility of the matrix material in the second solvent.

In any or all of the above embodiments, the active-rich domains have an average diameter of between 30 microns and 5 microns. In any or all of the above embodiments, the active-rich domains have an average diameter between 10 microns and 1 micron.

In any or all of the above embodiments, at least 80 wt % of said matrix material may comprise components with a molecular weight of less than 10,000 Daltons. In any or all of the above embodiments, at least 80 wt % of said matrix material may comprise components with a molecular weight of less than 5000 Daltons.

In any or all of the above embodiments, the matrix material may be selected from sugars, sugar alcohols, polyols, polyethers, amino acids, salts of amino acids, peptides, organic acids, salts of organic acids, and mixtures thereof. In any or all of the above embodiments, the matrix material may be selected from fructose, glucose, lactose, mannitol, trehalose, sucrose, raffinose, maltitol, lactitol, sorbitol, xylitol, erythritol, xylose, acorbose, melezitose, galactose, melibrose, isomaltose, malt beet sugar, corn sugar, high-fructose corn syrup, polydextrose, dextrans with molecular weights less than 10,000 Daltons, glycerol, ethylene glycol, propylene glycol, butanediol, glycine, leucine, serine, alanine, isoleucine, tri-leucine, oleic acid, citric acid, tartaric acid, edetic acid, malic acid, sodium citrate, low molecular-weight polyethylene glycols, poly amino acids, polyethylene glycol/polypropylene glycol copolymers, poloxamers, and mixtures thereof.

In any or all of the above embodiments, the solubility of the active in the second solvent is at least 2-fold the solubility of the active in the first solvent. In any or all of the above embodiments, the solubility of the active in the second solvent is at least 5-fold the solubility of the active in the first solvent.

In one embodiment, the active-rich domains are amorphous in the solid particles. In one embodiment, the active-rich domains are crystalline in the solid particles.

In another embodiment, the particles may undergo an endothermic irreversible heat flow associated with the active when measured by modulated differential scanning calorimetry (mDSC).

This disclosure also concerns products made by any or all of the above embodiments of the process.

DETAILED DESCRIPTION

Figure 1:
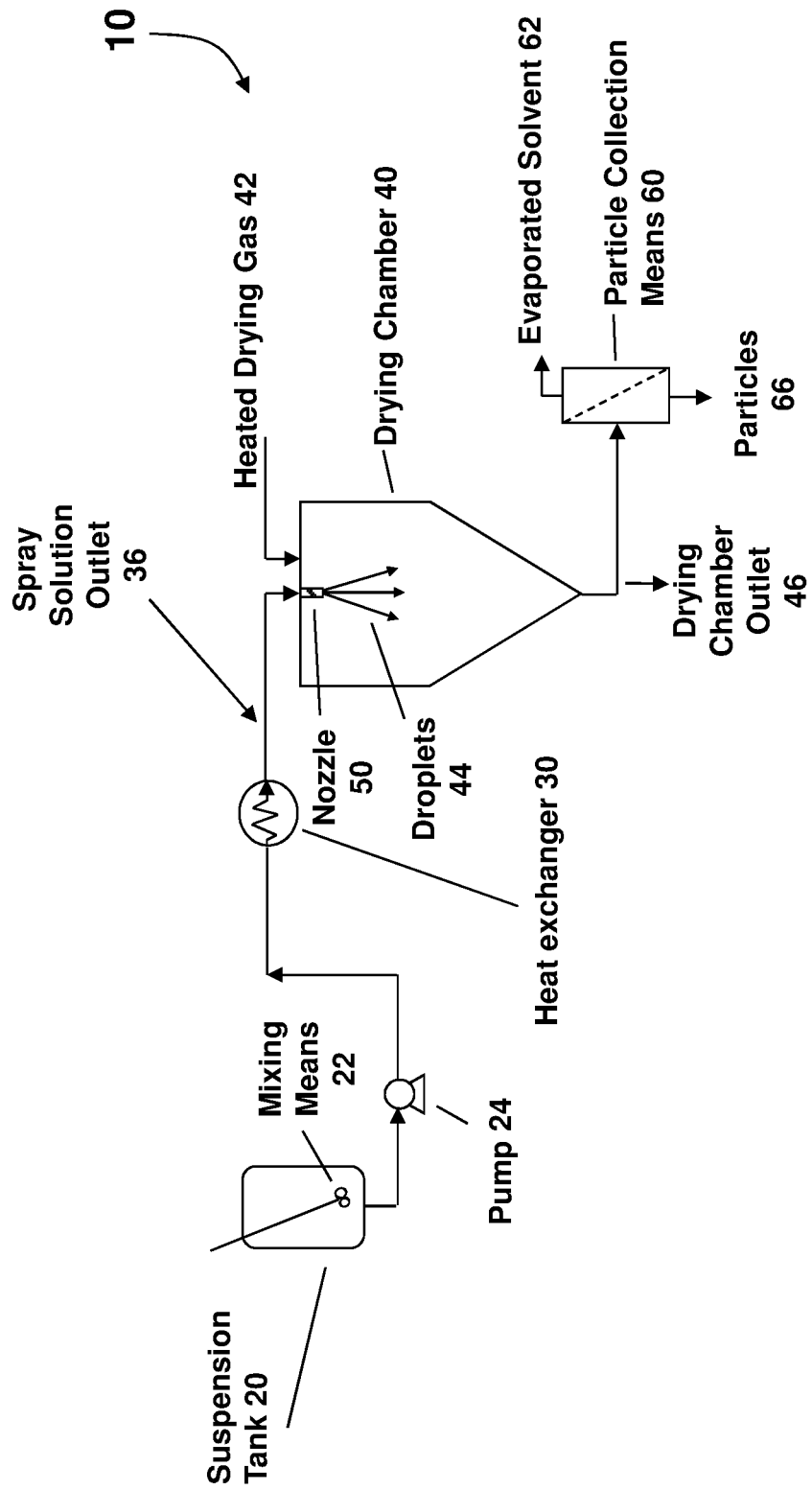
FIG. 1 shows one embodiment of a schematic of the process used to form the compositions claimed.

During a spray drying process, as droplets leave the spray nozzle, evaporative cooling and solvent evaporation takes place. This evaporation and associated cooling results in a supersaturated state for either active or matrix, or both due, at least in part, to a temperature decrease in the droplets. In one embodiment, the active becomes supersaturated in the drying droplets due to (1) a decrease in the solubility of the active in the first solvent and second solvent due to cooling of the droplet; (2) an increase in the concentration of the active due to evaporation of a portion of the solvents; and/or (3) a decrease in the solubility of the active in the solvents due to an increase in the ratio of the first solvent to the second solvent. Thus, the solution in the droplet becomes supersaturated with respect to the active as the second solvent is preferentially being evaporated from the droplet. The supersaturated state leads to precipitation of active or both the active and the matrix. This results in the formation of particles having active-rich domains and active-poor domains.

In formulating compositions for delivering active agents to an animal or patient, it is often desirable to form the compositions in which the active is present as small particles or domains. In order to promote the stability of delivery, dispersal and dissolution of the active, it is often desirable to disperse the small active particles in a matrix—the matrix typically comprising one or more pharmaceutically acceptable excipients. Such formulations can be delivered as dry powders, for example to the respiratory tract, can be dispersed in a vehicle for injection or oral delivery or can be incorporated into a solid dosage form such as a tablet or capsule.

As actives are typically obtained as relatively large and often poly-disperse particles or crystals, forming such compositions requires processing that is quite challenging. Typically, the particle size and often state of the active must be altered by unit processes such as dry milling, wet milling, dissolution followed by spray layering or spray drying or other such applications of mechanical, thermal or chemical energy. Depending on the specific active or actives being formulated and the specific delivery objective, it may be desirable for the small active domains to be in the amorphous state, crystalline state or a state in between these two extremes. States intermediate between the bulk, low-energy crystalline state and the amorphous state have been referred to by a range of terms including high-energy crystalline, nano-crystalline or "semi-ordered state".

In the case where it is desirable for the active to be in its most chemically and physically stable state, it is generally desirable for the active in the small domains to be essentially in the crystalline state. For example, for pharmaceuticals to be delivered to the respiratory tract as dry powders, actives are formulated as dry powders with a controlled aerodynamic diameter (AD). For the lower airways, powders generally will have ADs in the 1 to 5 micron range while for the upper airways, powders will generally have ADs in the 10 to 100 micron range. Often, it is desirable to deliver crystalline active to the respiratory tract but producing crystalline active powders with such controlled particle sizes by conventional spray drying, precipitation and milling processes is challenging.

In the case of formulating low-solubility active agents for oral delivery, the actives often show poor bioavailability or irregular absorption, the degree of poor bioavailability or irregularity being affected by factors such as dose level, fed state of the patient, and form of the drug. Increasing the bioavailability of low-solubility active agents has been the subject of much research. Increasing bioavailability hinges on improving the dissolution rate or concentration of the active agent in solution to improve absorption.

The dissolution rate can be increased by decreasing the size of active particles or domains. In cases where decreasing domain or particle size is sufficient to achieve adequate dissolution rates, the crystalline form of the active may be preferred due to its chemical and physical stability. In cases where an increase in the solubility of the active is required, a high-energy crystalline or nano-crystalline form or an amorphous form may be selected. The amorphous form of a low-solubility active agent that is capable of existing in either the crystalline or amorphous form may temporarily provide a greater aqueous concentration of active agent relative to the equilibrium concentration obtained by dissolution of the crystalline active agent in a use environment. It is believed that such amorphous forms of the active agent may dissolve more rapidly than the crystalline form, often dissolving faster than the active agent can precipitate from solution. As a result, the amorphous form may temporarily provide a greater than equilibrium concentration of active agent in solution.

While such amorphous forms may show initially enhanced concentration of the active agent in a use environment, nevertheless the improved concentration is often short-lived. Typically, the initially enhanced active agent concentration is only temporary and quickly returns to the lower equilibrium concentration.

One problem with using the amorphous form of an active agent is that the solid active agent may not be stable physically in the amorphous form. Often the crystalline form of the active agent has a lower free energy, and thus over time the amorphous drug will tend to crystallize. The rate of crystallization may be influenced by storage conditions, such as temperature and humidity, as well as the constituents of the composition. As a result, the active agent can crystallize or precipitate as a slow-dissolving solid, resulting in poor bioavailability.

A problem often encountered when attempting to formulate actives as small or nano-sized amorphous or crystalline particles or domains is maintaining their small size as they often have a tendency to agglomerate to larger particle sizes during processing, storage or during delivery and dissolution. This can be overcome by dispersing the active particles in an appropriate matrix. One object of the present disclosure is to provide methods, processes and formulations that can produce small domains of active dispersed in a matrix.

Definitions

Various embodiments are disclosed herein. The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Unless otherwise indicated, all numbers expressing quantities of ingredients, properties such as molecular weight, percentages, measurements, ratios, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Embodiments of the disclosed process include an active agent and a matrix material.

Active Agents

Embodiments of the disclosed process are suitable for use with any biologically active compound desired to be administered to a patient in need of the active agent. The compositions may contain one or more active agents. As used herein, by "active" or "active agent" is meant a drug, medicament, pharmaceutical, therapeutic agent, nutraceutical, or other compound that may be desired to be administered to the body. The active may be a "small molecule," generally having a molecular weight of 3000 Daltons or less.

The active agent may be highly water soluble (i.e., greater than 30 mg/mL at 25° C.), sparingly water soluble (i.e., 5-30 mg/mL), or a low-solubility active agent (i.e., less than 5 mg/mL). In one embodiment, the active agent is a "low-solubility active agent," and the active agent has a solubility in water (at 25° C.) of less than 5 mg/mL. In another embodiment, the active agent may have an even lower water solubility, such as less than 1 mg/mL, less than 0.1 mg/mL (100 µg/mL), less than 0.01 mg/mL (10 µg/mL), and even less than 0.005 mg/mL (5 µg/mL) at a pH of 6.5 and 25° C.

In one embodiment, the active has a solubility in the second solvent at the temperature $T_2$ that is greater than the solubility of the active in the first solvent at the temperature $T_2$. In one embodiment, the active has a solubility in the second solvent at the temperature $T_2$ that is at least 1.25-fold the solubility of the active in first solvent at the temperature $T_2$. In one embodiment, the active has a solubility in the second solvent at the temperature $T_2$ that is at least 2-fold the solubility of the active in first solvent at the temperature $T_2$. When the temperature $T_2$ is greater than the ambient-pressure boiling point of the second solvent, the following procedure may be used to determine the solubility of the active at the temperature $T_2$. A quantity of the active is added to the second solvent at temperature $T_1$, which is less than the ambient pressure boiling point of the second solvent, typically as a suspension of active particles in the second solvent at temperature $T_1$. This mixture is then placed into an appropriate pressure vessel with a sight glass for observing the contents of the pressure vessel. The pressure vessel is then heated to temperature $T_2$, and the contents observed either visually or using an analytical device, such as for measuring turbidity. When no solid particles are observed in the pressure vessel, the active has a higher solubility in the second solvent at $T_2$ than at $T_1$. The same procedures can be used to test the solubility of the active in the first solvent at temperature $T_2$.

In one embodiment, the solubility of the active in the second solvent is at least 1.25-fold the solubility of the active in the first solvent. In another embodiment, the solubility of the active in the second solvent is at least 2-fold the solubility of the active in the first solvent. In another embodiment, the solubility of the active in the second solvent is at least 3-fold the solubility of the active in the first solvent. In another embodiment, the solubility of the active in the second solvent is at least 5-fold the solubility of the active in the first solvent. In still another embodiment, the solubility of the active in the second solvent is at least 10-fold the solubility of the active in the first solvent.

The active agent should be understood to include the non-ionized form of the active agent, pharmaceutically acceptable salts of the active agent, or any other pharmaceutically acceptable forms of the active agent. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms, co-crystals, and prodrugs.

Examples of classes of active agents include, but are not limited to, compounds for use in the following therapeutic areas: antihypertensives, antianxiety agents, antiarrythmia agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, cholesteryl ester transfer protein inhibitors, triglyceride-reducing agents, antiobesity agents, autoimmune disorder agents, anti-impotence agents, antibacterial, anthelmintics, antihelminthics, antifungal agents, hypnotic agents, anti-Parkinsonism agents, anti-Alzheimer's disease agents, antibiotics, anti-angiogenesis agents, anti-glaucoma agents, anti-depressants, bronchodilators, glucocorticoids, steroids, and mixtures thereof.

In various embodiments, active agents for use in the disclosed process and products depend on the target state of matter. In one embodiment, the small active domains are substantially in the amorphous state. In one embodiment, at least 60 wt % of the active domains are amorphous. In another embodiment, at least 80 wt % of the active domains are amorphous. In still another embodiment, at least 90 wt % of the active domains are amorphous. In yet another embodiment, essentially all of the active domains are amorphous. In this embodiment the amorphous form of the active may be relatively stable. In another embodiment, the actives are those for which no crystalline state has been observed. In this embodiment, crystalline states may be known but some ionized states and ion pairs may not be known to crystallize. In other cases the amorphous form may be stable because the free energy of crystallization is very low. Such compounds generally have a melting point $T_m$ that is only somewhat higher than the glass transition temperature ($T_g$) of the amorphous form. Thus in one embodiment, compounds are those where $T_m-T_g$ is less than 80° C. or even less than 60° C. In other embodiments, the amorphous form may be stable because its $T_g$ is very high. Thus, the compounds for forming compositions with amorphous active domains are those with $T_g$s greater than 80° C., or greater than 60° C.

In many embodiments, it is desired to form powders wherein the small active domains are substantially in the crystalline state. In such cases, the crystalline state of the active may be stable and kinetically accessible relative to the amorphous state. In one embodiment, the active will have one or more crystalline states. In some embodiments, the active will have at least one crystalline state wherein the crystal has a melting point of at least 50° C. or even greater than 70° C.

In addition, in one embodiment, actives for forming crystalline domains are those for which the melting point, $T_m$, for at least one crystalline state is substantially higher than the glass transition temperature, $T_g$, of the amorphous state of the active. In one embodiment the $T_m$ is at least 40° C. greater than the $T_g$, or at least 60° C. greater than the $T_g$.

In one embodiment, the amorphous active crystallizes when it is exposed to temperatures above its $T_g$. In practice, such actives may be identified by conducting a differential scanning calorimetry (DSC) experiment. In general, it has been observed that when a sample of amorphous active is tested by increasing the temperature of the sample at a constant rate—typically 1 to 10 degrees C./min—that first a $T_g$ will be observed as a relatively sharp increase in heat capacity. Then, for some compounds—those actives that have a tendency to easily crystallize from the amorphous state—an exothermic peak will be observed indicating that the compound has crystallized. For such compounds, as the temperature increases further, an endothermic peak will be observed at the melting temperature, $T_m$, of the crystalline form of the compound. For many compounds this crystallization above the $T_g$ is not observed.

Thus, in one embodiment, compounds show an exothermic crystallization event at a temperature, $T_c$, above the $T_g$.

In some embodiments, to promote separation of the solids in the droplets into active-rich and active-poor domains it is generally desirable to select actives and second solvent combinations for which the active is highly soluble in the second solvent. In some embodiments, to promote separation of the solids in the droplets into active-rich and active-poor domains, it is generally desirable to select actives and second solvent combinations for which the active has a relatively high solubility in the second solvent. In particular, the active has a relatively low solubility in the first solvent compared to its solubility in the second solvent. In one embodiment, the active has a solubility in the second solvent that is at least 2-fold the solubility of the active in the first solvent. In other embodiments, the active has a solubility in the second solvent that is at least 2.5-fold, at least 3-fold, at least 3.5-fold, at least 4-fold, at least 4.5-fold, or at least 5-fold the solubility of the active in the first solvent.

Matrix Materials

The disclosed process includes at least one matrix material. By "matrix material" is generally meant a material of one or more pharmaceutically acceptable excipients in which the small active domains are mixed or dispersed. In general, the matrix material is chosen such that the small active domains formed by the process of the present invention have the desired size and physical state. In addition, the matrix material can aid in keeping the small active domains from aggregating and upon dissolution in a dosing vehicle or a use environment such as gastro-intestinal (GI) fluid, lung fluid, or plasma, the matrix material can aid in the dissolution process. The matrix material constitutes from 0.1 wt % to 99 wt % of the combined mass of the active agent and matrix material. When it is desirable for the matrix material to prevent aggregation of the active domains into larger aggregates, the matrix material constitutes more than 20% or even more than 40% of the combined mass of the active agent and matrix material. In some embodiments, the matrix material simply holds the active domains together to form a larger particle and constitutes less than 20%, or even less than 10% of the combined mass.

In one embodiment, the matrix material comprises components with a molecular weight of less than 10,000 Daltons, less than 5000 Daltons, or even less than 2000 Daltons.

To promote domain separation of the solids in the spray solution into active-rich domains and active-poor domains, it is generally desirable to select matrix materials that have a high solubility in the first solvent. Specifically, the solubility of the matrix material in the first solvent at $T_2$ should be greater than its solubility in the second solvent at $T_2$. Thus, as the second solvent evaporates from the droplets in the spray dryer more quickly than the first solvent evaporates, the droplets become enriched in the first solvent. This generally results in the solvent mixture becoming a better solvent for the matrix material and a poorer solvent for the active. Procedures for measuring the solubility of matrix materials at $T_2$ would be performed as measuring the solubility of the active agents, as described previously.

In one embodiment, the matrix material has a solubility in the first solvent that is at least 2-fold the solubility of the matrix material in the second solvent. In other embodiments, the matrix material has a solubility in the first solvent that is at least 2.5-fold, at least 3-fold, at least 3.5-fold, at least 4-fold, at least 4.5-fold, or at least 5-fold the solubility of the matrix material in the second solvent.

Generally, the first solvent has a lower ambient pressure boiling point than the second solvent, making it less volatile than the second solvent. In one embodiment, the first solvent has an ambient pressure boiling point that is at least 10° C. greater than the ambient pressure boiling point of the second solvent. In another embodiment, the first solvent has an ambient pressure boiling point that is at least 20° C. greater than the ambient pressure boiling point of the second solvent.

For example, when the first solvent is chosen to be water, the matrix materials should be more soluble in water than in the second solvent. In addition, the matrix material should not inhibit the separation of the active into small active-rich domains as the droplets and resulting particles form. Thus, matrix materials are those that have high mobility under the conditions of the drying droplet or particle. In general, "high mobility" matrix materials have low $T_g$ values and low molecular weights. In addition, matrix materials are those in which the active has poor solubility. That is, the solubility of the active in the matrix material at the conditions of the drying droplet or particle generally is lower than the mass percent of the active relative to the combined mass of the active agent and the matrix material. Because the mobility of high-molecular-weight polymers is typically low and the $T_g$ of high molecular weight polymers is typically high, the matrix materials typically have a low molecular weight. Specifically, in one embodiment, at least 80% of the matrix material comprises components that have a molecular weight average of less than 10,000 Daltons, less than 5000 Daltons, less than 2000 Daltons, or even less than 1000 Daltons.

Thus, again using water as an exemplary first solvent, matrix materials are those that have high solubility in the first solvent and generally having molecular weights below 10,000 Daltons. Examples of classes of matrix materials include sugars, sugar alcohols, polyols, polyethers, amino acids, salts of amino acids, peptides, organic acids, salts of organic acids, and mixtures thereof. Specific examples of sugars and sugar alcohols include, but are not limited to, fructose, glucose, lactose, mannitol, trehalose, sucrose, raffinose, maltitol, lactitol, sorbitol, xylitol, erythritol, xylose, acorbose, melezitose, galactose, melibrose, isomaltose, and mixtures thereof. Natural sugar extracts include, but are not limited to, malt beet sugar, corn sugar, high-fructose corn syrup, and sugar oligomers, such as polydextrose, dextrans with molecular weights less than 10,000 Daltons, and mixtures thereof. Exemplary polyols include glycerol, sorbitol, ethylene glycol, propylene glycol, butanediol, and other oligomers. Exemplary amino acids and salts of amino acids include glycine, leucine, serine, alanine, isoleucine, tri-leucine, and mixtures thereof. Exemplary organic acids and salts of organic acids include oleic acid, citric acid, tartaric acid, edetic acid, malic acid, sodium citrate, and mixtures thereof. Low molecular-weight oligomers are suitable including polyethylene glycols, poly amino acids or peptides and copolymers such as polyethylene glycol/polypropylene glycol copolymers, poloxamers, and mixtures thereof. In one embodiment, the matrix material is selected from fructose, glucose, lactose, mannitol, trehalose, sucrose, raffinose, maltitol, lactitol, sorbitol, xylitol, erythritol, xylose, acorbose, melezitose, galactose, melibrose, isomaltose, malt beet sugar, corn sugar, high-fructose corn syrup, polydextrose, dextrans with molecular weights less than 10,000 Daltons, glycerol, ethylene glycol, propylene glycol, butanediol, glycine, leucine, serine, alanine, isoleucine, tri-leucine, oleic acid, citric acid, tartaric acid, edetic acid, malic acid, sodium citrate, low molecular-weight polyethylene glycols having molecular weights of less than 10,000 Daltons, poly amino acids, polyethylene glycol/polypropylene glycol copolymers, poloxamers, and mixtures thereof. In another embodiment, the matrix material is selected from fructose, glucose, lactose, mannitol, trehalose, sucrose, raffinose, maltitol, lactitol, sorbitol, xylitol, erythritol, xylose, acorbose, melezitose, galactose, melibrose, isomaltose, malt beet sugar, corn sugar, high-fructose corn syrup, polydextrose, dextrans with molecular weights less than 10,000 Daltons, and mixtures thereof. In still another embodiment, the matrix material is selected from glycine, leucine, serine, alanine, isoleucine, tri-leucine, oleic acid, citric acid, tartaric acid, edetic acid, malic acid, sodium citrate, and mixtures thereof.

Although high molecular weight polymers—above 5000 to 10,000 Daltons—should generally not comprise the bulk of the matrix material, small amounts may be added—up to 20 wt % of the matrix material—to improve the properties of the final powder.

Optionally, other materials may be added to the matrix material to improve the properties of the resulting powder. Optional additives may include surfactants, lipids, binders, disintegrants, and the like.

Processes for Forming the Compositions

The term spray drying is used conventionally and broadly refers to processes involving breaking up liquid mixtures into small droplets (atomization) and rapidly removing solvent from the mixture in a container (drying chamber) where there is a strong driving force for evaporation of solvent from the droplets. The strong driving force for solvent evaporation is generally provided by maintaining the partial pressure of solvent in the spray drying apparatus well below the vapor pressure of the solvent at the temperature of the drying droplets. This is accomplished by (1) mixing the liquid droplets with a warm drying gas, (2) maintaining the pressure in the spray drying apparatus at a partial vacuum (e.g., 0.01 atm to 0.50 atm), or (3) both.

Generally, the temperature and flow rate of the drying gas is chosen so that the droplets of spray solution are dry enough by the time they reach the wall of the apparatus that they are essentially solid, form a fine powder, and do not appreciably coat or stick to the apparatus wall. As used herein, the term "essentially solid" refers to particles that comprise less than 10 wt % solvent based on the total weight of the particles. The actual length of time to achieve this level of dryness depends on the size of the droplets and the conditions at which the process is operated. Average droplet sizes may range from 1 μm to 500 μm in diameter, the size being dependent on the desired particle size of the spray dried powder.

Turning to the drawings, wherein the same numerals refer to like elements, there is shown in FIG. 1 an apparatus 10 suitable for performing embodiments of the disclosed process. In the following discussion it is assumed that the spray drying apparatus is cylindrical. However, the dryer may take any other cross-sectional shape suitable for spray drying a spray solution, including square, rectangular, and octagonal, among others. The spray drying apparatus is also depicted as having one nozzle. However, multiple nozzles can be included in the spray drying apparatus to achieve higher throughput of the spray solution.

The apparatus shown in FIG. 1 comprises a feed suspension tank 20, a heat exchanger 30, a drying chamber 40, a nozzle 50, and a particle-collection means 60. In one embodiment, the process is performed as follows. An active agent and the matrix material are combined with a first solvent and a second solvent in the feed suspension tank 20 to form a feed suspension. The feed suspension is initially at a temperature $T_1$, which is below the ambient-pressure boiling point of the solvents. Temperature $T_1$ is also below either $T_A$, the temperature at which the active agent solubility equals the active agent concentration in the solvents, or $T_M$, the temperature at which the matrix material solubility equals the matrix material concentration in the solvents. At $T_1$, at least a portion of the active agent, a portion of the matrix material, or a portion of both the active agent and the matrix material are suspended, that is not dissolved, in the solvents. In one embodiment, $T_1$ is less than 80° C. In one embodiment, $T_1$ is less than 70° C. In one embodiment, $T_1$ is less than 60° C., or less than 50° C., or less than 40° C.

An optional mixing means 22 may be used to keep the feed suspension more homogeneous while processing. When the solvent is flammable, oxygen is normally excluded from all parts of the drying apparatus. In particular, an inert gas, such as nitrogen, helium, argon, and the like is often used to fill the void space in the feed suspension tank for safety reasons.

As used herein, the term "feed suspension" means a composition comprising an active agent, the matrix material, a first solvent, and a second solvent, wherein at least a portion of the active agent, a portion of the matrix material, and/or a portion of both active agent and matrix material are suspended or not dissolved in the solvents. In one embodiment, the feed suspension consists essentially of an active agent, the matrix material, and the solvents. In still another embodiment, the feed suspension consists of an active agent, the matrix material, and the solvents. It will be recognized that in such feed suspensions, a portion of the active agent and the matrix material may dissolve up to their solubility limits at the temperature of the feed suspension.

The feed suspension includes a first solvent and a second solvent. Generally, the first solvent has an ambient-pressure boiling point that is greater than the ambient-pressure boiling point of the second solvent. In one embodiment, the first solvent has an ambient-pressure boiling point that is at least 10° C. greater than the second solvent. In other embodiments, the first solvent has an ambient-pressure boiling point that is at least 20° C. greater than the second solvent. The first solvent may have an even greater ambient-pressure boiling point, such as 30° C. greater, or 40° C. greater, or even 50° C. greater than the ambient-pressure boiling point of the second solvent.

Exemplary second solvents include methanol, acetone, tetrahydrofuran (THF), ethanol, isopropyl alcohol (IPA), methylene chloride, carbon tetrachloride, trichloroethane, hexane, heptane, n-propanol, ethyl acetate, acetonitrile, diethyl ether, and mixtures and combinations thereof.

Exemplary first solvents include water, dimethyl sulfoxide (DMSO), dimethylacetamide (DMAc), n-methylpyrrolidone (NMP), ethylene glycol, propylene glycol, heptane, n-propanol, isopropyl alcohol, toluene, benzyl alcohol, and mixtures and combinations thereof.

Some solvents, such as IPA may, in different situations, serve as either the second solvent or the first solvent. For example, when water (boiling point of 100° C.) is the first solvent, IPA (boiling point of 82° C.) may serve as the second solvent. For example when acetone (boiling point of 56° C.) is the second solvent, IPA may serve as the first solvent.

In one embodiment, at least a portion of the first solvent and the second solvent is removed from the droplets to form a solid composition. In another embodiment, a sufficient quantity of the first solvent and the second solvent is removed to form solid particles. In another embodiment, a major portion of the solvents are removed so as to form solid particles. In still another embodiment, substantially all of the solvents are removed so as to form solid particles. In one embodiment, residual solvent may be removed from the particles using a secondary drying process.

Spray solution temperature $T_2$ is greater than feed suspension temperature $T_1$. In one embodiment, the feed suspension is maintained in the feed suspension tank at the temperature $T_1$ until it is transferred via pump 24 to heat exchanger 30. To prevent unwanted vaporization/boiling of the solvents in the spray solution, pump 24 increases the pressure of the spray solution such that the pressure of the spray solution at spray solution outlet 36 is greater than the vapor pressure of the solvents at temperature $T_2$. The temperature of the spray solution when it enters the nozzle 50 is generally near $T_2$. In one embodiment, $T_2$ is greater than $T_1+40°$ C. In one embodiment, $T_2$ is greater than $T_1+50°$ C. In one embodiment, $T_2$ is greater than $T_1+60°$ C., or greater than $T_1+70°$ C., or greater than $T_1+80°$ C. In one embodiment, $T_2$ is greater than $T_4$.

In one embodiment, the active agent and the matrix material are both soluble in the solvents at temperature $T_2$. By "soluble" is meant that at equilibrium, essentially all of the active agent and matrix material would dissolve in the solvents at temperature $T_2$. In the case of the active agent, the term "dissolved" has the conventional meaning, indicating that the active agent is not present as a solid and has gone into solution. In the case of matrix materials, the term "soluble" can take a broader definition. For some matrix materials, such as polymers, the term dissolved can mean the polymer has gone into solution, or it can mean the polymer is dispersed or highly swollen with the solvent such that it acts as if it were in solution.

During the spray drying process, as the droplets leave the nozzle, evaporative cooling and solvent evaporation takes place. This evaporation and associated cooling results in a supersaturated state for either active or matrix, or both due to a temperature decrease in the droplets. In one embodiment, the active becomes supersaturated in the drying droplets due to (1) a decrease in the solubility of the active in the solvents due to cooling of the droplet; (2) an increase in the concentration of the active due to evaporation of a portion of the solvents; (3) a decrease in the solubility of the active in the solvents due to an increase in the ratio of the first solvent to the second solvent. Thus, the solution in the droplet becomes even more supersaturated with respect to the active as the second solvent and good solvent for the active is preferentially being evaporated from the droplet. The supersaturated state leads to precipitation of active or both of active and the matrix. This results in the formation of particles having active-rich domains and active-poor domains.

In one embodiment, the solubility of the matrix material in the first solvent at $T_2$ is greater than the solubility of the matrix material in the second solvent at $T_2$, and the solubility of the active agent in the second solvent at $T_2$ is greater than the solubility of the active agent in the first solvent at $T_2$.

In one embodiment, the pump 24 increases the pressure of the spray solution to a pressure ranging from 2 atm to 400 atm. In another embodiment, the pressure of the spray solution as it exits the heat exchanger 30 is greater than 10 atm.

The heat exchanger 30 may be of any design wherein heat is transferred to the feed suspension resulting in an increase in temperature. In one embodiment, the heat exchanger 30 is an indirect heat exchanger, wherein a heating fluid is in contact with the feed suspension through a heat-transfer surface. Exemplary indirect heat exchangers include tube-in-tube devices and tube-in-shell devices, both well-known in the art. The heat exchanger 30 may also be a direct heat exchanger, in which a heating fluid, such as steam, is injected directly into the feed suspension, resulting in an increase in the temperature of the feed suspension. In yet another embodiment, the feed suspension flows over a hot surface, such as a resistance heating element, resulting in an increase in temperature of the feed suspension. Other heating sources may also be used, such as microwaves and ultrasonic devices that can increase the temperature of the feed suspension.

The concentration of active agent and matrix material in the spray solution can be virtually any value that allows the practical conduct of the spray drying process. In particular, the concentration of matrix material and active agent must be low enough that the fluid directed to the atomization nozzle has a sufficiently low viscosity to be converted to droplets of about 500 microns or less. In one embodiment, the concentration of total solids (that is, active agent and matrix material) in the solvents is at least 0.5 wt %. The concentration of total solids in the solvents may be at least 1 wt %, at least 5 wt %, or even at least 10 wt % or more. In another embodiment, the concentration of active agent in the solvents is at least 1.25-fold the solubility of the active agent in the solvents at temperature $T_1$. The concentration of active agent in the solvents may be at least 1.5-fold, at least 2.0-fold, or even 2.5-fold or more the solubility of the active agent in the solvents at temperature $T_1$.

In one embodiment, the residence time of the feed suspension in the heat exchanger 30 is minimized so as to limit the time the suspension/solution is exposed to elevated temperatures. Limiting the exposure to elevated temperatures is beneficial in some instances, such as when the active agent or the matrix material is unstable and made degrade at elevated temperatures. The residence time of the suspension/solution in the heat exchanger may be less than 10 minutes, less than 1 minute, less than 40 seconds, less than 30 seconds, or even less than 5 seconds.

The spray solution at the spray solution outlet 36 is directed to a nozzle 50 for atomizing the spray solution into droplets 44, such that the droplets are directed into drying chamber 40. The temperature of the spray solution when it enters the nozzle 50 is the spray temperature, designated as $T_3$. When it is desired to keep the active agent and matrix material dissolved in the spray solution, it is often desirable for $T_3$ to be at or near $T_2$. However, there are sometimes advantages to having $T_3$ significantly less than $T_2$. For example, degradation of the active agent may be reduced or atomization in certain nozzles may be more effective when $T_3$ is significantly less than $T_2$. In some cases, it is even desirable for $T_3$ to be sufficiently low that the active agent, the matrix material, or both the active agent and the matrix material are not completely soluble in the solvent. In such cases, the solution may be below the point at which the solutes are completely soluble for a sufficiently short time such that all the solutes remain in solution until the solution is atomized. Alternatively, the solution may be below the point at which the solutes are completely soluble for a sufficiently long time that one or more of the matrix material or the active agent may at least partially precipitate or crystallize from solution. In one embodiment, temperature $T_3$ is up to 5° C. less than $T_2$. In another embodiment, temperature $T_3$ is up to 20° C. less than $T_2$. In another embodiment, temperature $T_3$ is up to 50° C. less than $T_2$. In still another embodiment, both temperatures $T_2$ and $T_3$ are greater than the greater of $T_A$ and $T_M$. In one embodiment, temperatures $T_2$ and $T_3$ are at least 5° C. greater than the greater of $T_A$ and $T_M$. In another embodiment, temperatures $T_2$ and $T_3$ are at least 20° C. greater than the greater of $T_A$ and $T_M$. In yet another embodiment, temperatures $T_2$ and $T_3$ are at least 50° C. greater than the greater of $T_A$ and $T_M$.

In one embodiment, the apparatus 10 is designed such that the time the spray solution is at a temperature greater than $T_3$ is minimized. Minimizing the time that the spray solution is at a temperature greater than $T_3$ may be beneficial when the active agent or the matrix material is unstable and may degrade at elevated temperatures. This may be accomplished by locating the spray solution outlet 36 as close as possible to the nozzle 50. Alternatively, the size of the tubing or fluid connections between the spray solution outlet 36 and the nozzle 50 may be small, minimizing the volume of spray solution and reducing the time the spray solution is at a temperature greater than $T_3$. The time the spray solution is at a temperature greater than $T_3$ may be less than 10 minutes, less than 1 minute, less than 40 seconds, less than 30 seconds, less than 10 seconds, or even less than 2 seconds.

In one embodiment, a pressure nozzle is effective in embodiments of the disclosed processes. In another embodiment, a 2-fluid nozzle is used. In still another embodiment, a flash nozzle is used, as described below.

The drying chamber 40 also has a source of drying gas 42 which is combined with the droplets 44 in the drying chamber 40. In the drying chamber 40, at least a portion of the solvents are removed from the droplets to form a plurality of particles comprising the active agent and the matrix material. Generally, it is desired that the droplets are sufficiently dry by the time they come in contact with the drying chamber surface that they do not coat or substantially stick to the chamber surfaces.

The particles, along with the evaporated solvent and drying gas, exit the drying chamber at outlet 46, and are directed to a particle-collection means 60. Suitable particle-collection means include cyclones, filters, electrostatic particle collectors, and the like. In the particle-collection means 60, the evaporated solvent and drying gas 62 are separated from the plurality of particles 66, allowing for collection of the particles.

The particles may be of any desired size. In one embodiment, the particles have an average diameter ranging from 0.5 µm to 500 µm. In another embodiment, the particles have a diameter ranging from 0.5 µm to 100 µm. In another embodiment, the particles have an average diameter of greater than 10 µm. In still another embodiment, the particles have an average diameter of greater than 20 µm. In still another embodiment, the particles have an average diameter of greater than 30 µm. In yet another embodiment, the particles have a mass median aerodynamic diameter ranging from 0.5 µm to 10 µm. In still another embodiment, the particles have a mass median aerodynamic diameter ranging from 1 µm to 5 µm.

In one embodiment, the concentration of solvent remaining in the solid particles when they are collected (that is, the concentration of residual solvent) is less than 10 wt % based on the total weight of the particles. In another embodiment, the concentration of residual solvent in the particles when they are collected is less than 5 wt %. In yet another embodiment, the concentration of residual solvent in the particles is less than 3 wt %. In another embodiment, a drying process subsequent to the spray-drying process may be used to remove residual solvent from the particles. Exemplary processes include tray drying, fluid-bed drying, vacuum drying, and the drying processes described in WO2006/079921 and WO2008/012617.

Figure 2:
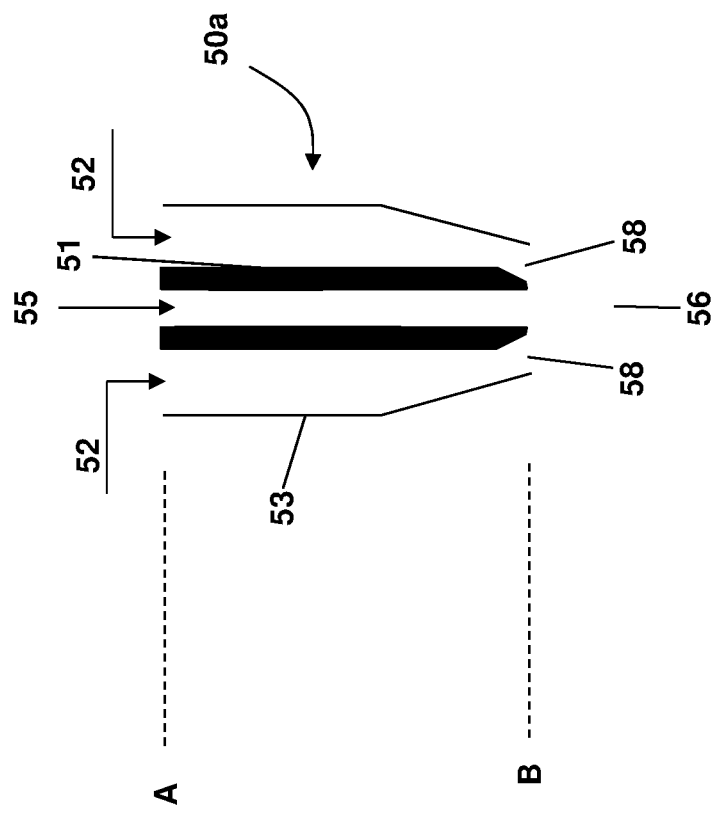
FIG. 2 shows a schematic of a flash nozzle.

In one embodiment, nozzle 50 is a flash nozzle 50a. There is shown in FIG. 2 a cross-sectional schematic of a flash nozzle 50a. Flash nozzle 50a consists of a central tube 51 and an outer tube 53. Central tube 51 is in fluid communication with the inflowing spray solution 55, while outer tube 53 is in fluid communication with a sweep gas 52. The flash nozzle 50a has an inlet end, represented by A, and an outlet end, represented by B. The spray solution 55 from the heat exchanger 30 (not shown in FIG. 2) enters central tube 51 at A. A sweep gas 52 enters outer tube 53 at A. As spray solution 55 travels through the central tube 51 from inlet A to outlet B, the pressure decreases due to pressure drop. Between the inlet A and outlet B, the pressure of the spray solution 55 decreases to a value that is less than the vapor pressure of the solvent in the spray solution, leading to the formation of vapor bubbles of the solvent (a process known as cavitation). By the time the spray solution 55 reaches outlet B of the central tube 51, it is a fluid 56 comprising droplets of spray solution and vapor-phase solvent. In one embodiment, the central tube 51 is coated with a non-stick coating. In another embodiment, the outer tube 53 is coated with a non-stick coating. In still another embodiment, the central tube 51 and the outer tube 53 are coated with a non-stick coating. Non-stick coatings include, for example, polytetrafluoroethylene (PTFE) or other suitable non-stick coatings.

The sweep gas 52 exiting through the outer tube outlet 58 is in fluid communication with the fluid 56 exiting through the central tube 51. The sweep gas 52 decreases the likelihood that solid material will form at the exit from the central tube 51 or the outer tube 53.

Characterization of the Compositions

The compositions made by embodiments of the disclosed process comprise active-rich domains and active-poor domains. In one embodiment, the composition comprises solid particles (e.g., particles that comprise less than 10 wt % solvent based on the total weight of the particles), each of the particles comprising a multiplicity of active-rich domains dispersed in an active-poor domain. In general, these active-poor domains comprise a matrix material. In another embodiment, the active-poor domains consist essentially of a matrix material. As used herein, "consist essentially of" means that the active-poor domains include at least 90 wt % matrix material and up to 10 wt % active and/or solvent. In yet another embodiment, the active-poor domains consist of the matrix material.

In one embodiment, the size of the active-rich domains has an average diameter of less than 50 microns. In another embodiment, the average size of the active-rich domains is less than 30 microns. In another embodiment, the average size of the active-rich domains is less than 20 microns, less than 10 microns, less than 5 microns. In another embodiment, the average size of the active-rich domains can be less than 2 microns, less than 1 micron, or even less than 0.7 microns. In another embodiment, the average size of the active-rich domains is between 30 microns and 5 microns. In still another embodiment, the average size of the active-rich domains is between 20 microns and 1 micron. In yet another embodiment, the average size of the active-rich domains is between 10 microns and 1 micron. In still another embodiment, the average size of the active-rich domains is between 5 microns and 0.7 microns.

In one embodiment, the active-rich domain is crystalline. Crystalline materials and crystalline active-rich domain sizes can be identified using modulated Differential Scanning Calorimetry (mDSC), Powder X-Ray Diffraction (PXRD), transmission electron microscopy (TEM), or scanning electron microscopy (SEM).

In one embodiment the active-rich domains are amorphous. The amorphous character of the active-rich domains can be determined by the PXRD pattern. Amorphous active-rich domains will generally show only broad diffraction peaks often described as the amorphous halo. The amount of amorphous drug in the active-rich domains may be quantitated by using an mDSC experiment. In some cases the mDSC scan of the product will show a glass transition associated with the amorphous form of the drug. By using appropriate controls (for example, amorphous active), the heat-capacity observed during the glass-transition temperature may be quantified and related to the total composition mass, resulting in a quantitative measure of the amount of amorphous active in the composition. As the active content of the amorphous active-rich domains approaches pure active, the Tg of these domains will approach the Tg of pure amorphous active, meaning within 30° C. of the pure amorphous active. Amorphous active-rich domains will exhibit a reversible heat flow associated with the amorphous nature of the active. Other techniques may also be used such as magic-angle spinning (MAS) solid-state nuclear magnetic resonance (NMR), which can be used to measure the size of amorphous active-rich domains. TEM and mDSC also may be used to measure the size of amorphous active-rich domains.

In other embodiments the active-rich domains are crystalline. By crystalline is meant that either 1) the PXRD of the composition displays scattering peaks that are sharper and narrower than those displayed by amorphous active, or 2) the mDSC scan of the composition displays an irreversible endothermic heat flow that is associated with the active rich domains.

In one embodiment, the active in the composition exhibits a powder x-ray diffraction (PXRD) pattern that is different from a PXRD pattern of the active agent in crystalline form. In another embodiment, the PXRD pattern of the composition has at least one peak that has a full width at half height of at least 1.1-fold that of an equivalent peak exhibited by the drug. In still another embodiment, the composition has a glass transition temperature that is different than the glass transition temperature of the active agent. In still another embodiment, the composition exhibits an onset or maximum in the melt endotherm that is at a lower temperature than the onset or maximum in the melt endotherm of said active agent in crystalline form.

Methods of Administration

In one embodiment, a method of treating an animal, including humans, in need of therapy comprises administering a composition comprising an active agent and a matrix material to an animal via a mode selected from the group consisting of oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal.

In one embodiment, the composition comprising an active agent and a matrix material is intended for oral, buccal, mucosal, or sublingual delivery. In this embodiment, the composition may be in the form of a powder that is incorporated into a suitable oral dosage form, such as tablets, capsules, caplets, multiparticulates, films, rods, suspensions, powders for suspension, and the like. Alternatively, the composition may be granulated prior to incorporation into a suitable dosage form.

In another embodiment, the composition comprising an active agent and a matrix material is intended for intravenous, intra-arterial, intramuscular, subcutaneous, intraperitoneal, intraarticular, infusion, intrathecal, intraocular, or intraurethral delivery. In this embodiment, the composition may be in the form of a suspension or solution, suitable for injection via a needle, for introduction to an IV bag or bottle, or delivered via an appropriate catheter to the intended delivery site. In one embodiment, the composition is formulated as a dry powder or solid, that is then reconstituted into a suspension or solution prior delivery. Formulating the composition as a dry powder or solid typically improves the chemical and/or physical stability of the composition. The dry powder or solid is then mixed with a liquid, such as water suitable for injection or other liquid, to form a suspension or solution that may then be delivered via the chosen route. In still another embodiment, the composition is delivered in the form of a depot that controls or otherwise modifies the rate of release of active agent from the depot. The depot may be formed prior to delivery, or may be formed in situ after delivery. Such depots can be in the form of suspensions or can be in the form of a monolith such as a film or rod. The active agent may be released very rapidly by dissolution of the composition when a soluble or enteric or dispersible form of the matrix is used. Alternatively, the active agent may be released over hours, days, or even many months by utilizing a poorly aqueous soluble matrix.

In another embodiment, the composition comprising an active agent and a matrix material is intended for topical delivery. In this embodiment, the composition may be formulated into appropriate creams, transdermal patches, and the like, as is well-known in the art.

In another embodiment, the composition comprising an active agent and a matrix material is intended for inhalation. As used herein, the term "inhalation" refers to delivery to a patient through the mouth and/or nose. In one embodiment, the dry powder suitable for inhalation is delivered to the "upper airways." The term "upper airways" refers to delivery to nasal, oral, pharyngeal, and/or laryngeal passages, including the nose, mouth, nasopharynx, oropharynx, and/or larynx. In another embodiment, the dry powder suitable for inhalation is delivered to the "lower airways." The term "lower airways" refers to delivery to the trachea, bronchi, bronchioles, alveolar ducts, alveolar sacs, and/or alveoli.

For pharmaceuticals to be delivered to the respiratory tract as dry powders, the actives are often formulated as dry powders with an aerodynamic diameter (AD). For the delivery to the lower airways, powders generally will have ADs in the 1 to 5 micron range. In one embodiment, the particles have an AD of 5 to 100 μm. In another embodiment, the particles have an AD of 10 to 70 μm. In yet another embodiment, the particles have an average diameter of 50 μm. In one embodiment, such particles are used in devices designed for delivery of particles to the upper airways. In another embodiment, such particles are used in devices designed for delivery of particles via the nose.

In one embodiment, the compositions may be formulated as a dry powder for use in a suitable inhalation device, such as a conventional dry powder inhaler. In another embodiment, the powders may be packaged in a packet suitable for insertion into a dry powder inhaler. Suitable dry powder inhalers typically rely on a burst of inspired air that is drawn through the unit to deliver the powder to the desired location. In another embodiment, the compositions may be administered as aqueous solutions or suspensions, or as solutions or suspensions in propellants, using, for example, a metered-dose inhaler. In this embodiment, the solution or suspension is aerosolized by liquid nebulizers employing either hydraulic or ultrasonic atomization. Compressor-driven nebulizers may also be employed, which may use a suitable propellant.

In another embodiment, the composition comprising an active agent and a matrix material is intended for ocular or intraaural delivery. In this embodiment, the compositions may be formulated into appropriate suspensions, creams, fluids, drops or other suitable forms for administration.

EXAMPLES

Active Agents

Fluticasone propionate, also known as (6S,8S,9R,10S, 11S,13S,14S,16R,17R)-6,9-difluoro-17-(((fluoromethyl) thio)carbonyl)-11-hydroxy-10,13,16-trimethyl-3-oxo-6,7,8, 9,10,11,12,13,14,15,16,17-dodecahydro-3H-cyclopenta[a] phenanthren-17-yl propionate, having the following structure, was used in the Examples.

Fluticasone has a melting temperature of 272° C., and a CLogP value of 3.8. It is practically insoluble in water.

Fenofibrate, also known as propan-2-yl 2-{4-[(4-chlorophenyl)carbonyl]phenoxy}-2-methylpropanoate, having the following structure, was used in the Examples.

Fenofibrate has a melting temperature of 80° C., and a CLogP value of 5.2. It is practically insoluble in water.

Example 1

A suspension of 4.43 wt % fluticasone/lactose at a temperature of 20 to 25° C. was prepared using a solvent of 50:50 acetone:water (wt:wt) by adding 1.8 g fluticasone and 0.21 g lactose to a container, and adding an appropriate amount of solvents to form a 90/10 fluticasone/lactose solution. In this example, water is the first solvent and acetone is the second solvent. Fluticasone is the active, and the matrix material is composed entirely of lactose. The solubility of fluticasone in water at 25° C. is less than 1 μg/mL. The lactose is soluble in water at 25° C. The solubility of fluticasone in acetone was 9 mg/ml at 25° C. The suspension, initially at a temperature of 20° C. to 25° C. was heated to a temperature of greater than 131° C. using a heat exchanger, and then sent to a Schlick 1.5 pressure nozzle at a flow rate of 20 g/min at 400 psig to form droplets. The temperature at the exit of the heat exchanger, just prior to the nozzle was determined as shown in Table 1. The suspension was mixed with drying gas at a drying gas flow rate of 500 g/min. The residence time of the solution in the heat exchanger was less than 1 minute. The droplets exited the nozzle into a drying chamber. The evaporated solvents and powder exited the drying chamber, and the particles were collected using a cyclone. The wet yield of the particles was 86 wt %. The resulting powders were vacuum dried overnight at room temperature. The other specific details of Example 1 are summarized in Table 1.

Examples 2 and 3

The procedures of Example 1 were followed except that the concentration of fluticasone and lactose were varied, as shown in Table 1. The spray conditions are also shown in Table 1, wherein the gas inlet temperature is the temperature of the drying gas, the solution temperature is temperature $T_3$, and the gas outlet temperature is measured at outlet 46 (FIG. 1).

TABLE 1

| Example | Composition | Solids Content (wt %) | Batch Size (g) | Wet Yield (wt %) | Gas Inlet Temp. (° C.) | Solution Temp. (° C.) | Gas Outlet Temp. (° C.) |
| --- | --- | --- | --- | --- | --- | --- | --- |
| 1 | 90/10 Fluticasone/Lactose | 4.43 | 2 | 86 | 163 | 131 | 60 |

TABLE 1-continued

| Example | Composition | Solids Content (wt %) | Batch Size (g) | Wet Yield (wt %) | Gas Inlet Temp. (° C.) | Solution Temp. (° C.) | Gas Outlet Temp. (° C.) |
|---|---|---|---|---|---|---|---|
| 2 | 50/50 Fluticasone/Lactose | 8 | 3 | 69 | 148 | 131 | 63 |
| 3 | 10/90 Fluticasone/Lactose | 29.4 | 10 | 57 | 140 | 131 | 60 |

Analysis of the Resulting Powders

Figure 3:
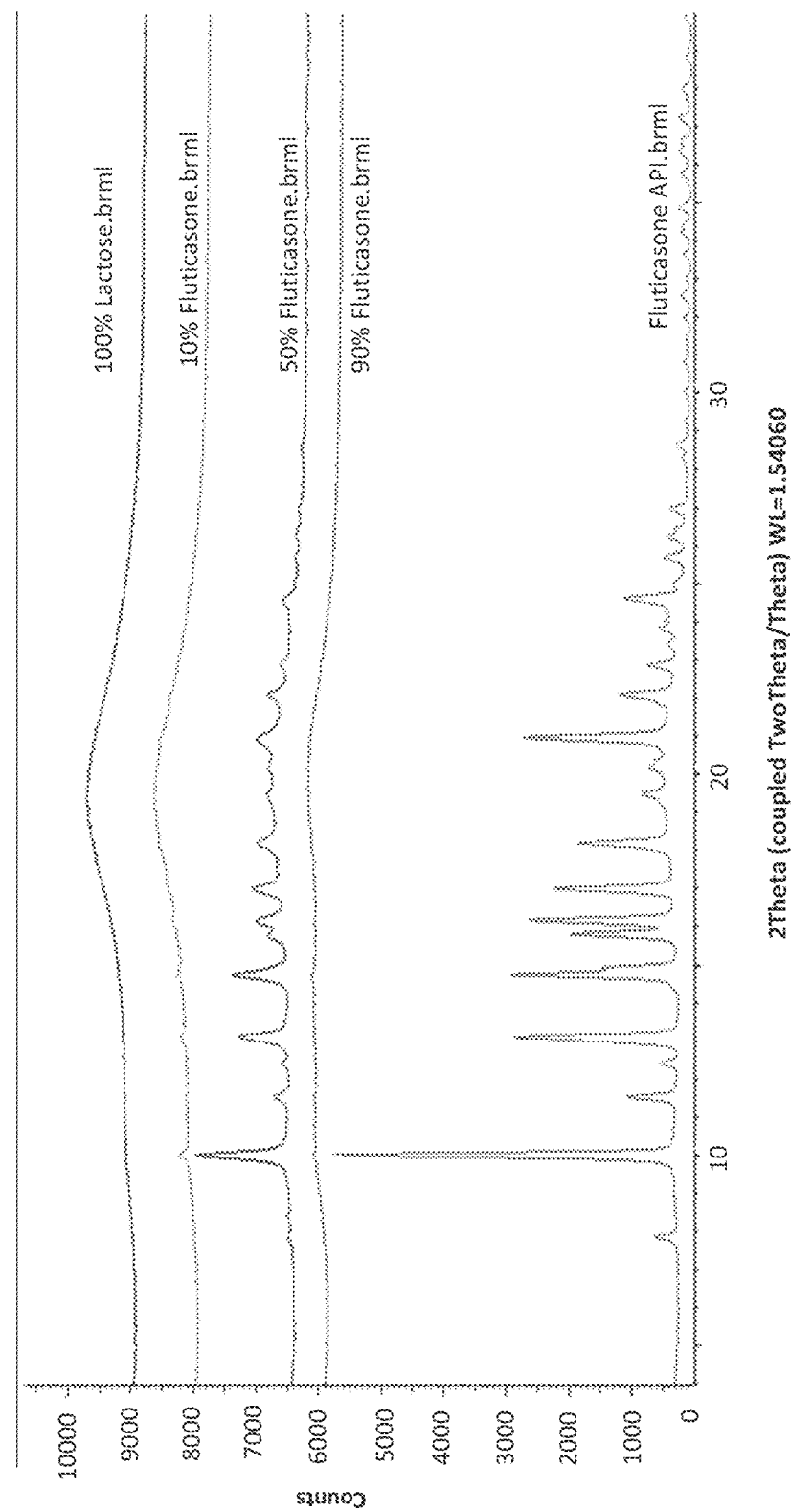
FIG. 3 shows the Powder X-ray Diffraction (PXRD) patterns for Examples 1-3: (1) 100% lactose, (2) 90% fluticasone, (3) 50% fluticasone, (4) 10% fluticasone, (5) fluticasone.

The materials of Examples 1-3, were evaluated by Powder X-Ray Diffraction (PXRD) using a Bruker AXS D8 Advance Diffractometer. Samples (approximately 100 mg) were packed in Lucite sample cups fitted with SiC 511) plates as the bottom of the cup to give no background signal. Samples were spun in the Ø plane at a rate of 30 rpm to minimize crystal orientation effects. The x-ray source ($KCu_\alpha$, $\lambda=1.54$ Å) was operated at a voltage of 45 kV and a current of 40 mA. Data for each sample were collected over a period of 27 minutes in continuous detector scan mode at a scan speed of 1.8 seconds/step and a step size of 0.04°/step. Diffractograms were collected over the 2θ range of 4° to 40°. FIG. 3 shows the diffraction patterns. As shown, all major crystalline peaks of fluticasone are present in the examples, with peak broadening observed in the 50% fluticasone sample.

Figure 4:
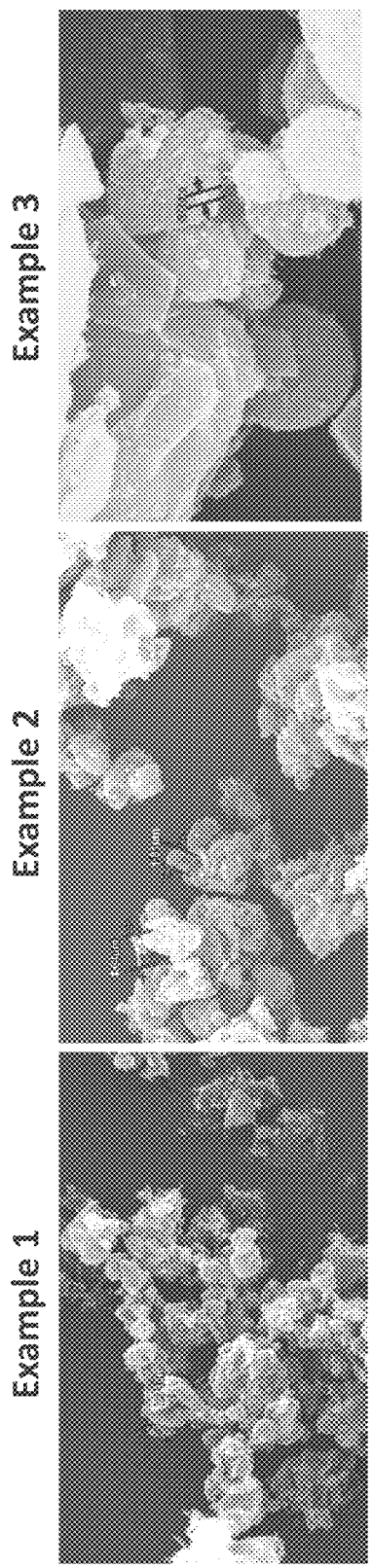
FIG. 4 shows scanning electron micrographs for Examples 1-3.

The powders were also examined by Scanning Electron Microscopy (SEM). The samples were prepared as follows: A scanning electron microscope (Hitachi S-3400Ne using S-3400 software at 4000× magnification) was used to study the morphology of the spray dried particles. Before observation with SEM, the powder was mounted on aluminum posts using double sided tape and sputter coated (Hummer 6.2) with AuPd. The SEM analysis was carried out at an accelerating voltage of 20 kV. The SEMs are shown in FIG. 4, which shows the powders formed irregular shaped particles of various sizes.

Example 4

A suspension of 3.99 wt % fenofibrate/lactose was prepared using a solvent of 50:50 acetone:water (wt:wt) by adding 1.8 g fenofibrate and 0.21 g lactose to a container, and adding an appropriate amount of solvents to form a 90/10 fenofibrate/lactose solution. Fenofibrate is the active, and the matrix material is composed entirely of lactose. The solubility of fenofibrate in water at 25° C. is less than 250 μg/mL. The lactose is soluble in water at 25° C. The fenofibrate is soluble in acetone at 25° C. The suspension, initially at ambient temperature was heated to greater than 131° C. using a heat exchanger, and then sent to a Schlick 1.5 pressure nozzle at a flow rate of 20 g/min at 400 psig to form droplets. The temperature at the exit of the heat exchanger, just prior to the nozzle was determined as shown in Table 2. The suspension was mixed with drying gas at a drying gas flow rate of 500 g/min. The droplets exited the nozzle into a drying chamber. The evaporated solvents and powder exited the drying chamber, and the particles were collected using a cyclone. The wet yield of the particles was 7.4 wt %. The resulting powders were vacuum dried overnight at room temperature. The other specific details of Example 4 are summarized in Table 2.

Examples 5 and 6

The procedures of Example 4 were followed except that the concentration of fenofibrate and lactose were varied, as shown in Table 2. The spray conditions are also shown in Table 2.

TABLE 2

| Example | Composition | Batch Size (g) | Solids Content (wt %) | Wet Yield (wt %) | Gas Inlet Temp. (° C.) | Solution Temp. (° C.) | Gas Outlet Temp. (° C.) |
|---|---|---|---|---|---|---|---|
| 4 | 90/10 Fenofibrate/Lactose | 2 | 4.43 | 7.4 | 150 | 131 | 60 |
| 5 | 50/50 Fenofibrate/Lactose | 4 | 8 | 11 | 148 | 132 | 60 |
| 6 | 10/90 Fenofibrate/Lactose | 20 | 29.4 | 36 | 162 | 128 | 60 |

Analysis of the Powders

Figure 5:
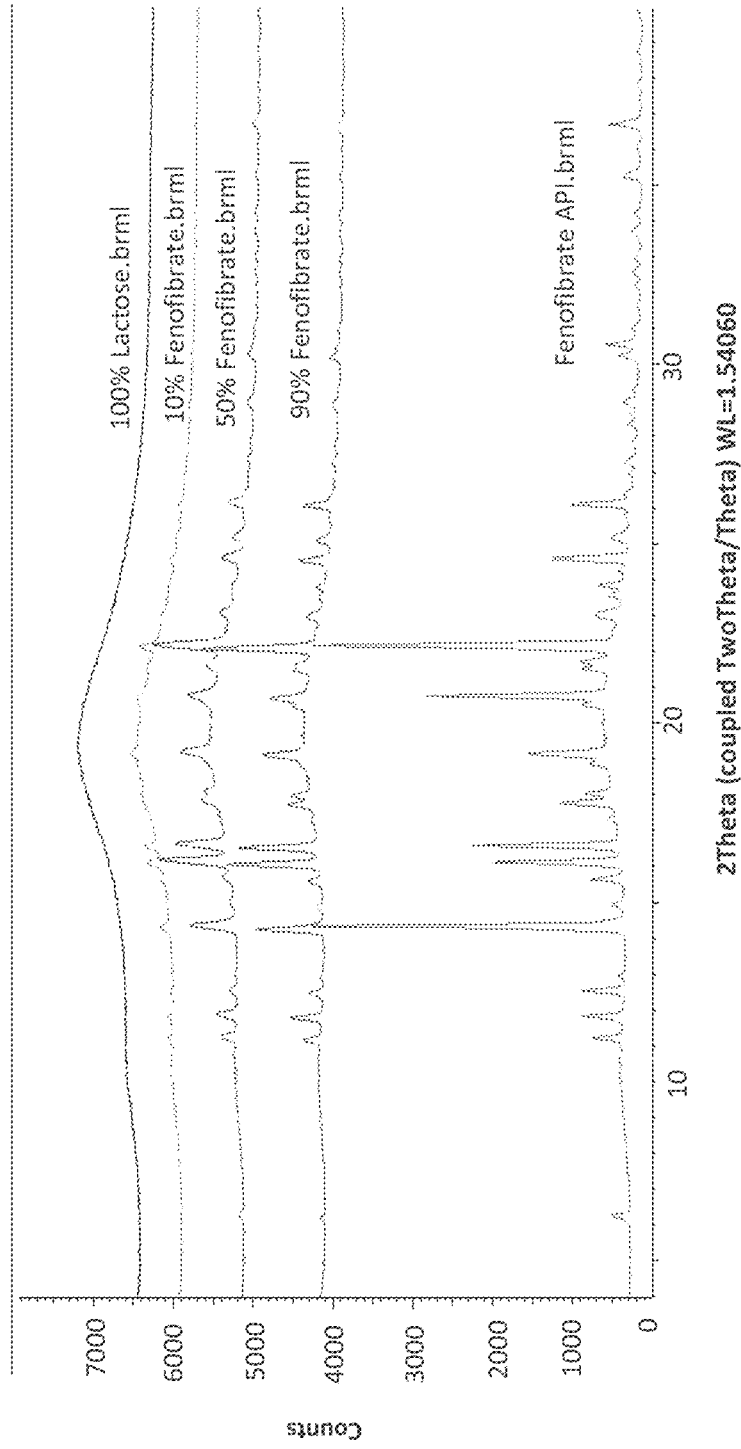
FIG. 5 shows the PXRD pattern for Examples 4-6: (1) 100% lactose, (2) 90% fenofibrate, (3) 50% fenofibrate, (4) 10% fenofibrate, (5) fenofibrate.

The Examples 4-6 were evaluated by Powder X-Ray Diffraction (PXRD) using the same procedures as described for Examples 1-3. FIG. 5 shows the diffraction patterns. As shown, all major crystalline peaks of fenofibrate are present in the samples, with peak broadening observed in the 90% and 50% fenofibrate samples.

Figure 6:
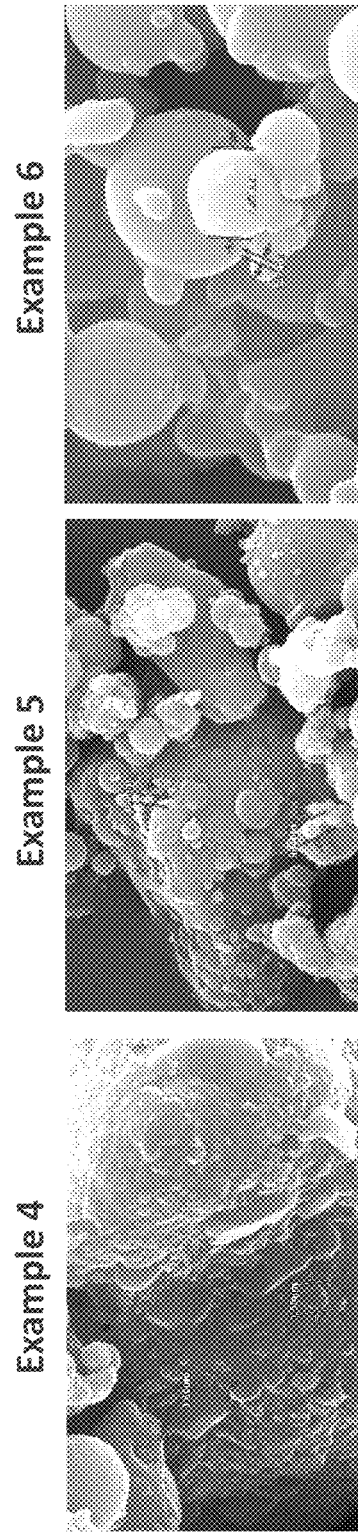
FIG. 6 shows scanning electron micrographs for Examples 4-6.

The powders were also examined by Scanning Electron Microscopy. The samples were prepared as described in Examples 1-3. The SEMs are shown in FIG. 6, and show relatively smooth particles, having irregular shapes and sizes.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A spray drying process for forming a composition providing an active and a matrix material, comprising:

a) forming and maintaining a suspension at a temperature $T_1$ in a feed suspension tank, the suspension comprising said active, said matrix material, a first solvent, and a second solvent, wherein the first solvent is water, and the second solvent is methanol, acetone, tetrahydrofuran, ethanol, isopropyl alcohol, ethyl acetate, acetonitrile, or any combination thereof;

b) heating said suspension in a heat exchanger to a temperature $T_2$, which is at least 40° C. greater than $T_1$, and a pressure $P_1$ greater than a vapor pressure of the first and second solvents at the temperature $T_2$, and wherein the residence time of the suspension in the heat exchanger is less than 10 minutes, thereby preventing unwanted vaporization or boiling of the first and second solvents, such that each of said active and said matrix material dissolves so as to form a spray solution;

c) subsequently atomizing said spray solution to form droplets;

d) drying said droplets by removing at least a portion of said first solvent, and at least a portion of said second solvent to form solid particles; and e) collecting said solid particles, said solid particles having active-rich domains and active-poor domains, the matrix material having a solubility in the first solvent at a temperature $T_2$ that is greater than the solubility of the matrix material in the second solvent at the temperature $T_2$, the active having a solubility in the second solvent at the temperature $T_2$ that is greater than the solubility of the active in the first solvent at the temperature $T_2$, the ambient-pressure boiling point of the first solvent being greater than the ambient-pressure boiling point of the second solvent; and wherein the second solvent evaporates more quickly from the droplets than the first solvent so that the active precipitates during the drying of the droplets at a rate that is initially faster than the rate at which the matrix material precipitates, creating the active-rich domains and the active-poor domains in the solid particles.

2. The process of claim 1 wherein the ambient-pressure boiling point of the first solvent is at least 10° C. greater than the ambient-pressure boiling point of the second solvent.

3. The process of claim 1 wherein the ambient-pressure boiling point of the first solvent is at least 20° C. greater than the ambient-pressure boiling point of the second solvent.

4. The process of claim 1 wherein said matrix material has a solubility in the first solvent that is at least 2-fold the solubility of the matrix material in the second solvent.

5. The process of claim 1 wherein said matrix material has a solubility in the first solvent that is at least 5-fold the solubility of the matrix material in the second solvent.

6. The process of claim 1 wherein said active-rich domains have an average diameter between 30 microns and 5 microns.

7. The process of claim 1 wherein said active-rich domains have an average diameter between 10 microns and 1 micron.

8. The process of claim 1 wherein at least 80 wt % of said matrix material comprises components with a molecular weight of less than 10,000 Daltons.

9. The process of claim 1 wherein at least 80 wt % of said matrix material comprises components with a molecular weight of less than 5000 Daltons.

10. A spray drying process for forming a composition providing an active and a matrix material, comprising:

a) forming and maintaining a suspension at a temperature $T_1$ in a feed suspension tank, the suspension comprising said active, said matrix material, a first solvent, and a second solvent, wherein said matrix material is selected from sugars, sugar alcohols, polyols, polyethers, amino acids, salts of amino acids, peptides, organic acids, salts of organic acids, and mixtures thereof, the first solvent is water, and the second solvent is methanol, acetone, tetrahydrofuran, ethanol, isopropyl alcohol, ethyl acetate, acetonitrile, or any combination thereof;

b) heating said suspension in a heat exchanger to a temperature $T_2$, which is at least 40° C. greater than $T_1$, and a pressure $P_1$ greater than a vapor pressure of the first and second solvents at the temperature $T_2$, and wherein the residence time of the suspension in the heat exchanger is less than 10 minutes, thereby preventing unwanted vaporization or boiling of the first and second solvents, such that each of said active and said matrix material dissolves so as to form a spray solution;

c) subsequently atomizing said spray solution to form droplets;

d) drying said droplets by removing at least a portion of said first solvent, and at least a portion of said second solvent to form solid particles; and e) collecting said solid particles, said solid particles having active-rich domains and active-poor domains, the matrix material having a solubility in the first solvent at a temperature $T_2$ that is greater than the solubility of the matrix material in the second solvent at the temperature $T_2$, the active having a solubility in the second solvent at the temperature $T_2$ that is greater than the solubility of the active in the first solvent at the temperature $T_2$, the ambient-pressure boiling point of the first solvent being greater than the ambient-pressure boiling point of the second solvent; and wherein the second solvent evaporates more quickly from the droplets than the first solvent so that the active precipitates during the drying of the droplets at a rate that is initially faster than the rate at which the matrix material precipitates, creating the active-rich domains and the active-poor domains in the solid particles.

11. The process of claim 1 wherein said matrix material is selected from fructose, glucose, lactose, mannitol, trehalose, sucrose, raffinose, maltitol, lactitol, sorbitol, xylitol, erythritol, xylose, acorbose, melezitose, galactose, melibrose, isomaltose, malt beet sugar, corn sugar, high-fructose corn syrup, polydextrose, dextrans with molecular weights less than 10,000 Daltons, glycerol, ethylene glycol, propylene glycol, butanediol, glycine, leucine, serine, alanine, isoleucine, tri-leucine, oleic acid, citric acid, tartaric acid, edetic acid, malic acid, sodium citrate, low molecular-weight polyethylene glycols with molecular weights less than 10,000 Daltons, poly amino acids, polyethylene glycol/polypropylene glycol copolymers, poloxamers, and mixtures thereof.

12. The process of claim 1 wherein the solubility of the active in the second solvent is at least 2-fold the solubility of the active in the first solvent.

13. The process of claim 1 wherein the solubility of the active in the second solvent is at least 5-fold the solubility of the active in the first solvent.

14. The process of claim 1 wherein said active-rich domains are amorphous in said solid particles.

15. The process of claim 10 wherein said matrix material is selected from fructose, glucose, lactose, mannitol, trehalose, sucrose, raffinose, maltitol, lactitol, sorbitol, xylitol, erythritol, xylose, acorbose, melezitose, galactose, melibrose, isomaltose, malt beet sugar, corn sugar, high-fructose corn syrup, polydextrose, dextrans with molecular weights less than 10,000 Daltons, glycerol, ethylene glycol, propylene glycol, butanediol, glycine, leucine, serine, alanine, isoleucine, tri-leucine, oleic acid, citric acid, tartaric acid, edetic acid, malic acid, sodium citrate, low molecular-weight polyethylene glycols with molecular weights less than 10,000 Daltons, poly amino acids, polyethylene glycol/polypropylene glycol copolymers, poloxamers, and mixtures thereof.

\* \* \* \* \*